(12) United States Patent
Rezai et al.

(10) Patent No.: US 11,590,254 B2
(45) Date of Patent: Feb. 28, 2023

(54) ABSORBENT ARTICLES COMPRISING ENCAPSULATING AGENTS

(71) Applicant: The Procter & Gamble Company, Cincinnati, OH (US)

(72) Inventors: Ebrahim Rezai, Mason, OH (US); Timothy Alan Scavone, Loveland, OH (US); Joerg Andreas Mueller, Mechernich (DE); Sebastian Blanck, Huenfelden (DE); Dean Larry DuVal, Lebanon, OH (US); James Steven Riedeman, Cincinnati, OH (US); Victor Nicholas Vega, Cincinnati, OH (US); Michael P. Purdon, Hebron, KY (US); Peter Christopher Ellingson, Symmes Township, OH (US); Vincent Scott Stapp, Florence, KY (US); Marc Jennewein, Taunusstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 643 days.

(21) Appl. No.: 15/631,580

(22) Filed: Jun. 23, 2017

(65) Prior Publication Data
US 2018/0333515 A1  Nov. 22, 2018

Related U.S. Application Data

(60) Provisional application No. 62/405,470, filed on Oct. 7, 2016, provisional application No. 62/354,306, filed on Jun. 24, 2016.

(51) Int. Cl.
| | | |
|---|---|---|
| *A61L 15/46* | (2006.01) | |
| *A61L 15/28* | (2006.01) | |
| *A61L 15/20* | (2006.01) | |
| *A61L 15/60* | (2006.01) | |
| *B01J 20/24* | (2006.01) | |
| *B01J 20/28* | (2006.01) | |
| *B01J 20/32* | (2006.01) | |
| *C11B 9/00* | (2006.01) | |

(52) U.S. Cl.
CPC ............... *A61L 15/46* (2013.01); *A61L 15/20* (2013.01); *A61L 15/28* (2013.01); *A61L 15/60* (2013.01); *B01J 20/24* (2013.01); *B01J 20/28016* (2013.01); *B01J 20/3231* (2013.01); *C11B 9/0061* (2013.01); *A61L 2300/802* (2013.01)

(58) Field of Classification Search
CPC . A61L 15/28; A61L 15/60; B01J 20/24; B01J 20/28016; B01J 20/3231; C11B 9/0061
USPC ....................................................... 502/1, 401
See application file for complete search history.

(56) References Cited

U.S. PATENT DOCUMENTS

| | | | | |
|---|---|---|---|---|
| 5,654,422 | A | * | 8/1997 | Hirsenkorn ......... C08B 37/0012 536/103 |
| 2012/0157946 | A1 | | 6/2012 | Caputi et al. |
| 2014/0378920 | A1 | | 12/2014 | Scavone et al. |

FOREIGN PATENT DOCUMENTS

| | | | |
|---|---|---|---|
| WO | WO91/12029 | * | 8/1991 |
| WO | WO 98/26808 A2 | | 6/1998 |

OTHER PUBLICATIONS

PCT International Search Report, dated Sep. 28, 2017, 86 pages.

* cited by examiner

*Primary Examiner* — Colin W. Slifka
(74) *Attorney, Agent, or Firm* — Amanda Herman Berghauer; Gary J. Foose; George D. Leal

(57) ABSTRACT

An absorbent article comprising an absorbent gelling material (AGM) having an encapsulated compound of one or more odor controlling organic compounds disposed upon a surface thereof is described. Alternatively, an AGM particle comprising an encapsulated reactive compound of one or more odor controlling organic compounds disposed as a surface coating thereon is described. Additionally, a method to manufacture an absorbent article is described. The method provides for the steps of: a) providing a solution in a solvent system, the solution has an encapsulating agent and one or more odor controlling organic compounds as a surface coating; b) applying an amount of the solution to a surface of an AGM particle; and, c) incorporating the AGM particle having the solution applied thereto into the absorbent article.

15 Claims, No Drawings

11,590,254 B2

ABSORBENT ARTICLES COMPRISING ENCAPSULATING AGENTS

FIELD OF THE DISCLOSURE

The present disclosure relates to absorbent articles comprising encapsulating agents and processes for producing absorbent articles comprising encapsulating agents. More particularly, the present disclosure relates to absorbent articles such as diapers, incontinence articles, catamenial devices, and the like, having a water-activatable, a pressure sensitive or friable-activatable, and/or a diffusion-activatable encapsulating compound disposed therein and processes for manufacturing these absorbent articles.

BACKGROUND OF THE DISCLOSURE

Absorbent articles according to the present disclosure are articles which can be used to absorb any type of fluid. Absorbent hygienic articles are commonly used to absorb and in some cases retain bodily fluids and other exudates excreted by the human or animal body, such as urine, menses, blood, fecal materials, mucus, chemicals, or any type of fluid waste. Paper towels, wipes, facial tissues toilet paper and other absorbent articles may be used also to absorb kitchen and food residues and/or any kind of dirt or waste. In many cases the absorbed materials, can be malodorant or can generate malodors with time while the article is still being used or after it has been disposed of or thrown in the trash.

Materials for controlling and reducing malodors in absorbent articles such as activated carbon, zeolites, silica, and the like have been used to trap volatile malodorant molecules in porous solids. Similarly, uncomplexed cyclodextrin molecules have been used to trap malodorant molecules by complexing them and reducing their volatility and act similarly to odor absorbers.

However current odor absorbers are not always satisfactory. Known odor absorbers must be complemented or replaced by odor controlling organic compounds to reduce the perception of malodors. Current odor controlling organic compounds are provided as fragrances (i.e., chemicals or blends of chemicals which stimulate the olfactory receptors providing a pleasant smell), odor masking compounds (i.e., compounds which stimulate the olfactory receptors so that unpleasant odors are perceived less or perceived as less disturbing), and reactive compounds (i.e., compounds which chemically react with the malodorant molecules altering their nature).

A menstrual or urine malodor when wearing an absorbent article is undesirable. Thus, there is a high demand for technologies that can counteract malodors in the fastest possible way.

SUMMARY OF THE DISCLOSURE

The present disclosure provides for an absorbent article comprising an absorbent gelling material (AGM) having an encapsulated compound of one or more odor controlling organic compounds disposed upon a surface thereof.

The present disclosure also provides for an AGM particle comprising an encapsulated reactive compound of one or more odor controlling organic compounds disposed as a surface coating thereon.

The present disclosure further provides for a method to manufacture an absorbent article. The method comprises the steps of: a) providing a solution in a solvent system, the solution comprising an encapsulating agent and one or more odor controlling organic compounds as a surface coating; b) applying an amount of the solution to a surface of an AGM particle; and, c) incorporating the AGM particle having the solution applied thereto into the absorbent article.

DETAILED DESCRIPTION OF THE DISCLOSURE

As used herein, an "absorbent article" refers to articles that absorb a fluid. Absorbent articles are typically disposable and can include paper towels, wipes, toilet paper, facial tissue, absorbent hygienic articles, absorbent articles used in the medical field such as wound dressings and surgical articles, absorbent articles used in food technology and conservation (e.g., fluid pads for meat, fish, and the like), absorbent articles used industrially to absorb fluids such as spilled chemicals, as well as the individual components of such exemplary absorbent articles which in and of themselves may also be absorbent, alone or in combination.

As used herein, "absorbent hygienic articles" generally refers to devices that absorb and contain body exudates, such as urine, menses, blood, and feces. "Disposable" is used herein to describe articles that are not intended to be laundered or otherwise restored or reused after a single use. Exemplary absorbent hygienic articles include diapers, toddler training pants, adult incontinence pants, pads or diapers, and feminine hygiene garments such as sanitary napkins, panty-liners, tampons, inter-labial articles, breast pads, hemorrhoid pads, and the like. Most absorbent hygienic articles (except those for internal use such as tampons) typically comprise a topsheet, a backsheet, and an absorbent core disposed between the topsheet and backsheet.

Absorbent hygienic articles and the components thereof (e.g., topsheet, backsheet, absorbent core, and any individual layers of these components) can have a body-facing surface and a garment-facing surface. A "body-facing surface" means that surface of the article or component thereof is intended to be worn toward or adjacent to the body of the wearer. The "garment-facing surface" is opposed thereto and is intended to be worn toward, or placed adjacent, to the wearer's undergarments when the disposable absorbent article is worn.

A "topsheet" is preferably compliant, soft feeling, and non-irritating to the wearer's skin and/or hair. Further, a topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials (e.g., apertured formed thermoplastic films, apertured plastic films, and hydroformed thermoplastic films), porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or a combination thereof. When the topsheet comprises a nonwoven web, the web may be manufactured by a wide number of techniques. For example, the web may be spun-bonded, carded, wet-laid, melt-blown, hydro-entangled, combinations of the above, or the like.

As used herein, the "backsheet" can be impervious to liquids (e.g., menses and/or urine) and can be manufactured from a thin plastic film, although other flexible materials may also be used such as nonwovens. As used herein, the term "flexible" refers to materials that are compliant and readily conform to the general shape and contours of the human body. A backsheet can prevent exudates absorbed and contained in the absorbent core from wetting articles that contact the absorbent article such as bedsheets, pants, pajamas and undergarments. A backsheet can also be vapor permeable ("breathable") and remain fluid impermeable. The backsheet may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Panty fastening means can be, for example, a layer of adhesive or mechanical means such as Velcro® or combination thereof. When an adhesive is present, typically a release paper is also present in order to protect the adhesive before use.

The backsheet and the topsheet can be positioned respectively adjacent the garment surface and the body surface of the absorbent core. The absorbent core can be joined with the topsheet, the backsheet, or both in any manner by attachment means known to those of skill in the art. Embodiments of the present disclosure are envisioned wherein portions of the entire absorbent core are unattached to either of the topsheet, the backsheet, or both.

As used herein, an "absorbent core" can be formed from any of the materials known to those of ordinary skill in the art. Exemplary materials include multiple plies of creped cellulose wadding, fluffed cellulose fibers, wood pulp fibers also known as air-felt, textile fibers, a blend of fibers, a mass or batt of fibers, air-laid webs of fibers, a web of polymeric fibers, and a blend of polymeric fibers. Other suitable absorbent core materials can include absorbent foams such as polyurethane foams or high internal phase emulsion ("HIPE") foams.

For some absorbent articles, the absorbent core can be relatively thin (e.g., less than about 5 mm in thickness, or less than about 3 mm, or less than about 1 mm) in thickness. Thickness can be determined by measuring the thickness at the midpoint along the longitudinal centerline of the pad by any means known in the art while under a uniform pressure of 1.72 kPa.

The absorbent core can comprise superabsorbent materials such as absorbent gelling materials (AGM), including AGM fibers (described infra). The absorbent core can therefore constitute a layer comprising superabsorbent material.

The absorbent article can comprise other additional components between the topsheet and absorbent core (e.g., a secondary topsheet or acquisition layer). A secondary topsheet or acquisition layer can comprise a tissue layer or a nonwoven, such as carded resin-bonded nonwovens, embossed carded resin-bonded nonwovens, high-loft carded resin-bonded nonwovens, carded through-air bonded nonwovens, carded thermo-bonded nonwovens, spunbonded nonwovens, and the like. A variety of fibers can be used in a secondary topsheet or acquisition layer, including natural fibers (e.g. wood pulp, cotton, wool, and the like), as well as biodegradable fibers (e.g., polylactic acid fibers), and synthetic fibers such as polyolefins (e.g., polyethylene and polypropylene), polyesters, polyamides, synthetic cellulosics (e.g., RAYON®, Lyocell®), cellulose acetate, bi-component fibers, and blends thereof. The basis weight of the secondary topsheet or acquisition layer can vary depending upon the desired application.

The absorbent article can comprise further components such as side cuffs, typically found in diapers, or side wings or side flaps, typically found in sanitary napkins.

Absorbent catamenial tampons are absorbent articles for internal use in the vagina and are typically made by a pledget comprising absorbent fibers compressed into a cylindrical shape. Tampons can be "digital tampons" when they have a self-sustaining shape and can be inserted with a finger or "applicator tampons" (e.g., tampons introduced using an applicator). Tampons can also comprise an extraction cord so to facilitate extraction from the vagina. These absorbent hygienic articles are preferably disposable after a single use.

Absorbent hygienic articles herein can be commercialized in packages containing a plurality of units, often the package is a plastic film or a carton box. Single units contained within the commercial package can be individually packaged or not.

Reactive Compounds

As used herein, a "reactive compound" can be generally described as odor controlling organic compounds introduced into an absorbent article in the form of complexes or as encapsulates. This can be beneficial because fragrances and odor masking compounds are volatile materials and lose efficacy due to evaporation from the absorbent articles during storage and use. Most reactive compounds are also volatile so encapsulating or forming cyclodextrin complexes can prevent their evaporation. Moreover, all reactive compounds (volatile and less volatile) are "reactive" and tend to have poor chemical stability.

Reactive compounds can be perfumed or non-perfuming. As used herein, a "perfume" is a mixture of fragrant essential oils or aroma compounds, fixatives and solvents used to give the human body, animals, food, objects, and living-spaces "a pleasant scent".

When odor controlling organic compounds are incorporated into absorbent articles they can be released from a complex, or an encapsulating compound, when the article contacts fluids to be absorbed. This is typically the moment at which malodors can start developing and at which the release of odor controlling compounds can be necessary.

Absorbent Gelling Material

As used herein, "Absorbent gelling materials" ("AGM"), also referred to as "Superabsorbant Polymers" refer to absorbent materials that are cross-linked polymeric materials that can absorb at least 10 times their weight of an aqueous 0.9% saline solution as measured using the Fluid Retention Capacity test (Nonwoven Standards Procedures NWSP 241.0.R2(15)). AGMs are typically used in particulate form so as to be flowable in a dry state. The term "particles" refers to granules, fibers, flakes, spheres, powders, platelets and other shapes and forms known to persons skilled in the art of superabsorbent polymer particles.

Exemplary particulate absorbent polymer materials can comprise poly(meth)acrylic acid polymers. However, starch-based particulate absorbent polymer materials may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. An AGM may comprise polyacrylates and polyacrylic acid polymers that are internally and/or surface cross-linked. AGMs can be internally cross-linked (i.e., the polymerization is carried out in the presence of compounds having two or more polymerizable groups which can be free-radically copolymerized into the polymer network). Exemplary AGMs (superabsorbent polymer particles) are described in WO2006/083584, WO2007/047598, WO2007/046052, WO2009/155265, WO2009/155264.

Encapsulating Compounds

Reactive compounds of the present disclosure can be encapsulated using any technique known in the art. "Encapsulation" as used herein is intended to encompass any technology that facilitates the introduction of a reactive compound into an absorbent article as a solid in a mixture with other materials which are called in general "encapsulating materials". Reactive compounds are prevented from contacting other materials to avoid unwanted reactions when encapsulated. Moreover, when encapsulated, evaporation of a reactive compound is prevented. All types of capsules are usable in the methods and articles of the present disclosure. Capsules can have any size, typically used in the art and suitable herein are nanocapsules, microcapsules, and larger capsules. In general, capsules can have a size such that their shorter diameter will be lower than 3 mm or lower than 1 mm.

Capsules can allow an encapsulated composition to release when it is needed. In the case of absorbent articles, this can correspond to at least three types of encapsulation compounds. Encapsulation compounds can include water activated/activatable encapsulating compounds (agents), friction activated/activatable compounds (agents), and diffusion activated/activatable compounds (agents).

Generally, a water activated/activatable encapsulating compound (agent) provides for the receipt of a liquid insult (e.g. when in absorbent hygienic articles menses or urine are discharged). In this case capsules comprise water soluble materials or materials that trigger a release of the encapsulated compound when contacted with water or a water-containing liquid.

Generally, a friction activated/activatable encapsulating compound (agent) provides for when pressure or force is exerted on the article (e.g. in the case of paper towels and wipes, or in the case when an absorbent hygienic article is worn during a period of high activity). For example, breakable capsules having a shell of rupturable polymeric film can be used.

Generally, a diffusion activated/activatable encapsulating compound (agent) provides for the constant egress of an encapsulated compound.

These three types of encapsulating compounds are not intended to be limiting examples. Any trigger (or combination of triggers) can be used to release the encapsulated compound from the capsule (e.g., pH change, evaporation, diffusion, temperature, humidity, light, etc.). The release of the encapsulated compound can be instantaneous or sustained over time, depending on need. A skilled person, based on the desired trigger action and release type, will be able to select an appropriate encapsulating material. Capsules can use different encapsulating materials such as those provided infra. Further, it is preferred that the AGM is not plasticized to prevent integration of the encapsulating compound into the AGM. It is believed that the prevention of plasticization (or swelling) of the AGM can provide the benefit of the preventing penetration of the encapsulating agent and odor controlling compound into the AGM particle and preventing agglomeration of the surface coated AGM particles.

As used herein, "plasticization" generally, refers to a change in the thermal and/or mechanical properties of a polymer that involves: (a) lowering of rigidity at room temperature; (b) lowering of the temperature at which substantial deformations can be effected with small forces; (c) increase of the elongation to break at room temperature; (d) increase of the impact strength down to the lowest temperature of serviceability. Plasticization can be determined mechanically by analysis by Differential Scanning calorimetry (DSC) and/or Dynamic Mechanical Analysis (DMA). The degree of plasticization would be understood by one of skill in the art to be related to the glass transition temperature, $T_g$, of the polymer.

1. Polymers

Polymeric materials can be used as encapsulating materials. Exemplary, but non-limiting polymers can include classical coacervates such as water soluble coacervates, partly soluble coacervates, or insoluble coacervates, charged polymers, neutral polymers, liquid crystals, hot melts, hydrogels, perfumed plastics, microcapsules, nano- and micro-latexes, polymeric film formers, and polymeric absorbents, polymeric adsorbents, combinations thereof, and the like. Polymeric capsules include, but are not limited to, matrix systems and/or reservoir systems.

Matrix systems generally provide for the encapsulated compound to be dissolved or dispersed in a polymer matrix or particle. For example, these compounds may be dispersed into the polymer prior to formulating into the product. Diffusion of the encapsulated compound from the polymer is a common trigger that allows or increases the rate of compound release from a polymeric matrix system that is deposited or applied to the desired surface although many other triggers may control compound release. Exemplary triggers can include absorption and/or adsorption into or onto polymeric particles, films, solutions, and the like. Exemplary polymeric particles can include nano- or micro-particles composed of organic materials (e.g., latexes). Exemplary particles include a wide range of materials such as polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems generally intend to keep the compound associated with the polymer until the moment or moments of release. Such polymers may also suppress the neat product odor and provide a bloom and/or longevity benefit depending on the rate of compound release. One of skill in the art will understand that there is preferably a balance between 1) in-product stability (keeping the compound inside carrier until needed) and 2) timely release during use. Matrix systems can also include hot melt adhesives and perfumed plastics.

Silicones are exemplary polymers that may be used as encapsulating materials and can provide compound release benefits. Exemplary silicones include polydimethylsiloxane and polyalkyldimethylsiloxanes.

Reservoir systems, also known as a core-shell type technology, can provide for the release of a compound surrounded by a release controlling membrane, which serves as a protective shell. The material inside the capsule is referred to as the core, internal phase, or fill, whereas the wall is sometimes called a shell, coating, or membrane. Depending on the type of shell materials, the capsules can be activated by different mechanisms (e.g., the coating can be soluble in water or soluble in water solutions having a certain pH). In certain embodiments of the present disclosure, reservoir capsules can have water insoluble shells and the core of the capsule is released upon mechanical activation.

Pressure sensitive capsules or friable capsules are examples of this technology. Friable capsules can be made in any sizes, and shapes, typically used are friable microcapsules. Any type of polymeric material can be used to make the shell of friable capsules, as well as any material can be used as a core material as known in the art. A skilled person will be able to determine which materials can be used to encapsulate certain core materials based on the knowledge available in the art concerning the compatibility of the materials (e.g., in general the shell material is selected so that core material will not act as a solvent on it). Friable microcapsules will be described in more detail. A skilled person will appreciate that the same type of materials and construction can be used to make large or small capsules.

Friable microcapsules are capsules where the outer shell is made from any polymer or mixture of polymers. Typical polymers that can be used to be comprised in the shell of a friable microcapsule include melamine-formaldehyde or urea-formaldehyde condensates, melamine-resorcinol or urea-resorcinol condensates, nylon, polyacrylates, polyethylenes, polyamides, polyamides, polystyrenes, polyisoprenes, polycarbonates, polyesters, polyureas, polyurethanes, polyolefins, polysaccharides, epoxy resins, vinyl polymers, silk, wool, gelatin, cellulose, proteins and mixture thereof as well as co-polymers comprising, as co monomers, monomers contained in these mentioned polymers.

Among the most stable friable microcapsules are those comprising polyoxymethyleneurea (PMU)-based polymers, melamine-formaldehyde based polymers, and polyacrylate based polymers.

In some embodiments the microcapsule outer shell material can include a polyacyrylate material. Any polymer or copolymer including acrylate or metacrylate monomers can be used in the articles and process of the present disclosure. In some embodiments the shell of the microcapsules comprises a polyacrylate copolymer or a polyacrylate random copolymer.

A friable microcapsule can be configured to release the core substance when the outer shell is ruptured. The rupture can be caused by a force applied to the outer shell during mechanical interactions. Friable microcapsules can have various fracture strengths. Each microcapsule can have an outer shell with a fracture strength ranging from 0.2-10.0 MPa, when measured according to the Fracture Strength Test Method described in U.S. patent application Ser. No. 61/703,587.

Each friable microcapsule has an outer shell and a core contained within the outer shell. Each friable microcapsule can be provided with a core-to-outer-shell ratio (in weight) ranging from about 99-1 to about 1-99, or from about 95-5 to about 10-90, or from about 50-50 to about 90-10. Additionally, friable microcapsules can have various outer shell thicknesses. In some embodiments the friable microcapsule can have an outer shell with a thickness ranging from about 1-300 nanometers or from about 2-200 nanometers.

For application to an anhydrous product such as an absorbent article, it can be preferred that the microcapsule be applied as an anhydrous particle. Such particles may be produced by spray drying. In the instances where friable microcapsules are spray dried, it can be preferable to apply these particles in a paste or slurry comprising a carrier vehicle. These particles may also be directly applied to the substrate as a powder without using a carrier vehicle. For example, the spray dried particles can be applied to an adhesive that is part of a peelable surface containing an adhesive. Peelable surfaces containing adhesives may include for example the panty fastening backsheet adhesive or the wings adhesive. When the surface is peeled away, a burst of fragrance is emitted and the fragrance can then be transferred to the clothing for added odor protection. Alternately, friable microcapsules can be delivered via an aqueous slurry to surfaces of the absorbent article and allowed to dry.

2. Starches

Starch encapsulation technology can facilitate the modification of properties of the compound to be encapsulated. For example, a liquid compound can be converted into a solid by adding starch. This can provide a benefit including increased retention for volatile compounds during product storage. Upon exposure to moisture, a release may be triggered. Another benefit allows the product formulator to select compounds or concentration of compounds that normally cannot be used without the presence of starch encapsulation.

Starch encapsulated compounds may be made by preparing a mixture comprising starch, water, acid and the compound(s) to be encapsulated. The acid is provided in an amount sufficient to lower the pH of the starch-water mixture by at least 0.25 units. The mixture can be spray dried forming the encapsulated compound(s). In the first step, an aqueous mixture is prepared comprising starch, water, the compound(s) to be encapsulated, and acid. The components may be added in any order, but typically the starch-water mixture is prepared first and subsequently, either sequentially or together, the acid and compound(s) to encapsulate are added. When they are added sequentially, the acid may be added prior to the ingredient for encapsulation. Alternatively, the acid is added after the ingredient for encapsulation. The concentration of starch in the aqueous mixture may be from as low as about 5 wt % or about 10 wt % to as high as about 60 wt % or even about 75 wt %. Generally, the concentration of starch in the mixture ranges from about 20 wt % to about 50 wt %, or about 25 wt % to about 40 wt %, in the aqueous mixture.

Suitable starches can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch and mixtures thereof. Modified starches may be particularly suitable for use in the present disclosure, and these include hydrolyzed starch, acid thinned starch, starch having hydrophobic groups, such as starch esters of long chain hydrocarbons ($C_5$ or greater), starch acetates, starch octenyl succinate, starch esters, such as starch octenyl succinates, and mixtures thereof.

The term "hydrolyzed starch" refers to oligosaccharide-type materials that can be obtained by acid and/or enzymatic hydrolysis of starches (e.g., corn starch). It may be preferred to include in the starch water-mixture (e.g., a starch ester). Modified starches comprising a starch derivative containing a hydrophobic group or both a hydrophobic and a hydrophilic group which has been degraded by at least one enzyme capable of cleaving the 1,4 linkages of the starch molecule from the non-reducing ends to produce short chained saccharides to provide high oxidation resistance while maintaining substantially high molecular weight portions of the starch base can be preferred. An aqueous starch mixture may also include a plasticizer for the starch. Exemplary hydrolyzed starches include monosaccharides, disaccharides, oligosaccharides, and maltodextrins, such as glucose, sucrose, sorbitol, gum arabic, guar gums, and maltodextrin.

The acid used in the process of the present disclosure may be any acid. Exemplary acids include sulfuric acid, nitric acid, hydrochloric acid, sulfamic acid, and phosphoric acid, carboxylic organic acids, combinations thereof, and the like. Exemplary organic acids comprising more than one carboxylic acid groups include citric acid, tartaric acid, maleic acid, malic acid, succinic acid, sebacic acid, adipic acid, itaconic acid, acetic acid, ascorbic acid, saturated acids, such as citric acid, combinations thereof, and the like can be suitable.

Following the formation of the aqueous mixture comprising starch, water, perfumes and acid, the mixture can be mixed under high shear to form an emulsion or dispersion of the target ingredient(s) for encapsulation in the aqueous starch solution.

Any suitable technique may then be used for the final stage of processing where the aqueous mixture including acid and perfumes is atomized and dried. Suitable techniques include, but are not limited to those known in the art including spray drying, extrusion, spray chilling/crystallization methods, fluid bed coating and the use of phase transfer catalysts to promote interfacial polymerization. Spray efficiencies may be increased by methods known in the art, such as by using high drying towers, lightly oiling the chamber walls, or using preconditioned air in which the moisture has been substantially removed.

3. Coated Capsules

One of skill in the art will recognize that the primary materials forming the capsule may be further encapsulated with a secondary coating material. Any of the capsule types discussed supra can be used with or without an additional secondary coating material.

An additional secondary coating material can help in reducing the scent perception, in reducing evaporation of volatile components over time (especially at elevated temperatures and humidity conditions), and in increasing chemical stability of the complexed compound by reducing the exposure of the complexed compounds (which in the present disclosure comprise highly reactive materials) to prematurely react or decompose so they are no longer functional or have a different odor character when activated. Additionally, using coated capsules can allow altering the release characteristic of the encapsulated material (slowing or accelerating its release, or changing the release trigger, for example introducing a pH trigger). Generally, any second material added or directly applied to a primary encapsulating material that accomplishes one or more of the above functions can be characterized as a coating. A secondary coating may be directly applied using a second process step following creation of the primary capsule, using a process such as prilling, or using any fluidized bed process to apply a secondary surface coating (i.e., a Wurster Coater).

Any suitable coating composition may be used as required. Exemplary coating compositions can include polysaccharides (e.g., unmodified starch, chemically modified starch, dextrins, cyclodextrin, cyclodextrin derivatives, and combinations thereof), natural and artificial/synthetic waxes, esters, ester derivatives, fatty acids, natural, synthetic, and chemically modified lipids, fatty alcohols, hydrocarbons (linear, branched, and/or petrolatum), enteric coating compositions (such as the Eudragit® series of Methacrylic acid co-polymers), polyvinyl alcohols, polyethylene glycols, silicones (for example, but not limited to silicone copolymers and functionalized silicones), surfactants, emulsifiers, polypropylene glycols, cellulose derivatives (methyl cellulose, hydroxypropyl cellulose), glycerin, mono- and di-glycerides, polyglycerol and polyglycerol esters and emulsifiers.

4. Complexed Compounds

A "complex" is intended as an "inclusion complex" within the meaning of IUPAC Compendium of Chemical Terminology 2nd Edition (1997) where the complexing agent is the host and the complexed compound is the "guest". Examples of complexing agents are cyclodextrins. As used herein, the term "cyclodextrin" includes any of the known cyclodextrins such as substituted and unsubstituted cyclodextrins containing from about six to about twelve glucose units, for example alpha-cyclodextrin, beta-cyclodextrin, gamma-cyclodextrin and/or their derivatives and/or mixtures thereof. For example, the cyclodextrin complex of the present disclosure can comprise cyclodextrin selected from the group consisting of beta-cyclodextrin, alpha-cyclodextrin, hydroxypropyl alpha-cyclodextrin, hydroxypropyl beta-cyclodextrin, methylated-alpha-cyclodextrin, methylated-beta-cyclodextrin, and mixtures thereof. Cyclodextrin complexes of compounds which are active against malodors can be prepared as known in the art for example using the kneading method described in U.S. Pat. Nos. 5,571,782 and 5,543,157 or by a spray drying method described in International Patent Publication No. WO2008/104690 A2. By way of non-limiting example, exemplary complexed compound can comprise a cyclodextrin provided as a "substituted cyclodextrin".

As known, cyclodextrins are a family of compounds where a number of glucose units are bound together in a ring shaped structure (cyclic oligosaccharides). More specifically cyclodextrins are formed by 5 or more α-D-glucopyranoside units linked through the carbon atoms in positions 1 and 4 on the glucose ring. Typically the number of glucose units forming each ring is from 6 to 12, and are most commonly those with 6, 7 or 8 glucose units, are called alpha-cyclodextrin, beta-cyclodextrin, and gamma-cyclodextrin respectively. Each glucose unit in cyclodextrin has three —OH groups bound to the carbon atoms in positions 2, 3 and 6.

As used herein, the term "substituted cyclodextrin" includes any cyclodextrin wherein one or more hydrogen atom of the —OH groups in positions 2, 3 and 6 of the glucose units is replaced by a substituent —R thus forming an —OR group. The average number of —R substituents for each glucose unit in a given sample represents the "degree of substitution" (DS) which is a number ranging from 0 to 3 where 0 corresponds to no substitutions (all —OH groups in position 2, 3 and 6 are present) and 3 to a complete substitution (all —OH groups in position 2, 3 and 6 are replaced by —OR groups). The average is calculated on a molar basis.

Absorbent articles of the present disclosure can comprise cyclodextrin complexes of one or more odor controlling organic compound wherein the cyclodextrin is a substituted cyclodextrin having a substitution degree (DS) of 0.4 or more —R substituents per molecule of cyclodextrin and wherein substitution in position 2 is 20% or above, in position 6 is 20% or above and in position 3 is 50% or below.

In a preferred aspect of this disclosure, the average degree of substitution ranges from between 0.4 and 2.5, or between 0.9 and 2, or between 1.2 and 1.8. In a preferred aspect of this disclosure, the substitution in position 2 can be between 20 and 90%, or between 45% and 80%. In a preferred aspect, the substitution in position 6 can be between 20 and 90%, or between 45% and 80%. This disclosure encompasses combinations of the aspects mentioned supra.

The —R substituents in the —OR groups can be selected from any substituent having a carbon atom in position 1 (thus forming an —O—C— bond with the oxygen atom). Suitable —R substituents may include carbon atoms chains which are saturated or unsaturated and can be straight or branched. For example, suitable —R substituents include saturated and straight chain C1-6 alkyl, hydroxyalkyl, and mixtures thereof. Particularly suitable —R substituents have a carbon chain of from 1 to 6 carbon atoms and are selected from alkyl, hydroxyalkyl, dihydroxyalkyl, carboxy-alkyl, aryl, maltosyl, allyl, benzyl, alkanoyl, and mixtures thereof, wherein the term "alkyl" encompasses both linear and branched alkyl chains.

Preferred —R substituents are propyl, ethyl, methyl, and hydroxypropyl. Different —R substituents can be present in the same substituted cyclodextrin sample, on the same cyclodextrin molecule, and even on the same cyclodextrin glucose unit. In a particularly useful aspect of the disclosure all the —R substituents are methyl substituents. In this case the substituted cyclodextrin is also called "methylated cyclodextrin."

It has been surprisingly found that cyclodextrin complexes according to the present disclosure release more rapidly the complexed molecule when the absorbent article is contacted with an aqueous fluid if compared with similar complexes wherein the cyclodextrin is not substituted or where the substitution is differently distributed between positions 2, 3 and 6.

For example a particularly suitable cyclodextrin material for the present disclosure is a methylated cyclodextrin having a DS of 0.4 or higher, or range from 0.4 to 2.5, or from 0.9 to 2, or from 1.2 to 1.8 and wherein at least 20%, or between 20% and 90%, or between 45% and 80% of the ~OH groups in positions 2 and 6, respectively, are methylated and wherein 50% or less of those in position 3 are methylated. The degree of substitution can be measured with gas chromatography as described below with reference to methyl substituents in β-Cyclodextrin.

Determination of Methyl Substituent Distribution

The Methyl Substituent Distribution in methylated β-cyclodextrin can be measured by gas chromatograph with split/splitless injection and flame ionization detection. The β-cyclodextrin can be hydrolyzed, reduced, and acetylated for analysis. Additionally, gas chromatography/mass spectrometry can be used to identify the acetylated products to confirm peak identity.

Derivatization reagents can have a purity of >99% except for borohydride (98%) (Sigma Aldrich or equivalent). 50 mg of methylated β-cyclodextrin and 5 mL of 2 M trifluoroacetic acid solution were added to a 50 mL round bottom flask with magnetic stir bar. The reaction vessel was fitted with a water cooled condenser and heated to reflux for 4 hours while stirring. After complete hydrolysis, the reaction mixture was evaporated under vacuum to dryness. Next, the hydrolysis product, 10 mL of ammonium hydroxide (32% in water), and 101 mg sodium borohydride (2.67 mmols) were stirred in a 50 mL round bottom flask at 40° C. for 2 hours. Residual sodium borohydride was quenched via dropwise addition of glacial acetic acid until the solution pH was in the range of 4.5 to 6. The resulting boric acid was removed via sequential additions of methanol (4×20 mL) to the reaction mixture followed by evaporation under vacuum at 40° C. The reaction product, 10 mL of pyridine, 36 mg of 4-dimethylaminopyridine (0.2947 mmols), and 630 µL acetic anhydride (630 µL, 6.6794 mmols) were added to a 50 mL round bottom flask with magnetic stir bar. The reaction was stirred vigorously at room temperature for 20 hours. The acetylated alditol products were extracted with 10 mL chloroform using a 60 mL separatory funnel and washed three times with 10 mL of deionized water. The chloroform extract was diluted (1:3) with chloroform, and sampled for gas chromatography analysis.

The GC analysis was performed on a 30 m long by 0.250 mm diameter column with 5% phenyl arylene methylpolysiloxane phase at a 1 µm film thickness (Agilent DBSMS or equivalent USP G27 phase). The GC inlet was set at 280° C. in Split mode (5:1 split, glass wool packed liner) with a 3 mL septum purge. A 1.5 mL column flow of helium was set at an oven temperature of 150° C. under constant flow conditions. The detector was set at 300° C. with flows set to the instrument manufacture's recommended conditions. The GC oven was programmed to begin at 150° C. for 1 min, then ramp at 15° C./min to 250° C., hold for 4 min at 250° C., then ramp at 10° C./min to 315° C. and a final hold of 1 min. 1 µL of the chloroform extract is injected for analysis. It is understood that one skilled in the art can slightly modify the chromatographic conditions to achieve the necessary separation as needed.

GC-MS analysis can be performed under the same chromatographic conditions as for the FID. The temperature for the MSD transfer line and detector were set to 280° C. and 300° C. respectively. The MSD was configured for electron ionization at −70 eV scanning from 35 m/z to 400 m/z with a scan rate of 257 msec/scan. The Total Ion Chromatogram was evaluated using the fragmentation data in Table 1 to assign retention order of the glucitol products. The retention order was then applied to the GC-FID chromatograms.

For quantification, each peak measured by GC-FID that is associated with a glucitol monomer is integrated to give a peak area. The areas are then used in Equations 1 and 2 to calculate the mole percent (mol %) of each glucitol monomer and reported to the nearest 0.1 mol %. The results from the example chromatogram in FIG. 1 are given in Table 1.

$$\text{mols glucitol } A = \text{mg } \beta \text{ cyclodextrin} \times \frac{FID \text{ area counts for glucitol } A}{\Sigma \ FID \text{ area counts of all glucitol monomers}} \times \frac{1}{MW_A} \quad \text{Eq. 1}$$

where:

$MW_A$=molecular weight of the acetylated glucitol; and, mg β-cyclodextrin is the starting mass of underivatized methyl β-cyclodextrin $$\text{mol \% glucitol } A = \frac{\text{mols glucitol } A}{\Sigma \text{ mols of all glucitol monomers}} \times 100\% \quad \text{Eq. 2}$$

Additionally, the mol % of particular substitutions can be calculated by addition of the individual mol %. For example, the mol % of all glucitols methylated at the 6 position (denoted in Table 1 as X6) would be the sum of the mol % of S2,6, S3,6, and S2,3,6.

The average degree of substitution was calculated according to Equation 3. The mol % for all glucitol monomers sharing the same number of methyl substituents (0, 1, 2, or, 3) were summed, multiplied by their respective methyl substituent number (0, 1, 2, or 3) and divided by 100. The result is reported to the nearest 0.1 mol %.

$$DS \text{ per glucose unit} = \frac{1}{100}\sum_{i=0}^{3} i \cdot \text{mol \%} \, x \qquad \text{Eq. 3}$$

where:

mol % x=summation of glucitol monomers having same number of methyl groups.

TABLE 1

Selected Fragments of Ionized D-Glucitol Acetates

| Compound | m/z | | | | | | | | | | | | | | | |
|---|---|---|---|---|---|---|---|---|---|---|---|---|---|---|---|---|
| | 99 | 113 | 117 | 129 | 145 | 157 | 159 | 161 | 189 | 217 | 231 | 233 | 261 | 289 | 305 | 333 |
| 2,3,6-Tri-O-methyl-D-glucitol, 1,4,5-triacetate | X | X | X | X | | | X | | | | | X | | | | |
| 2,6-Di-O-methyl-D-glucitol, 1,3,4,5-tetraacetate | | X | X | | | X | | | | X | | | | X | | |
| 3,6-Di-O-methyl-D-glucitol, 1,2,4,5-tetraacetate | X | X | | X | | X | X | | X | | | X | | | | |
| 2,3-Di-O-methyl-D-glucitol, 1,4,5,6-tetraacetate | X | | X | | | | X | X | | | X | | X | | X | |
| 6-O-methyl-D-glucitol, 1,2,3,4,5-pentaacetate | X | | | X | X | X | X | | | X | X | | | X | | X |
| 2-O-methyl-D-glucitol, 1,3,4,5,6-pentaacetate | | | X | X | | X | X | | | | X | | | | | X |
| 3-O-methyl-D-glucitol, 1,2,4,5,6-pentaacetate | X | | | X | X | | X | | X | X | X | | X | | | |
| D-glucitol hexaacetate | | | | | X | X | | | | | X | | | X | | |

X = Fragment present in mass spectra

TABLE 2

Substituent Distribution for Methylated β-cyclodextrin, Average Degree of Methylation of the O6 and O2 Positions, and the Average Degree of Substitution (DS) Per Glucose Unit.

| Substituent Distribution | mol % |
|---|---|
| Unsubstituted | 9.1 |
| S2 | 21.9 |
| S3 | 5.8 |
| S6 | 10.4 |
| S2, 3 | 13.7 |
| S2, 6 | 20.1 |
| S3, 6 | 6.1 |
| S2, 3, 6 | 12.8 |
| X6 | 49.5 |
| X2 | 68.6 |
| X3 | 38.5 |
| Avg. DS per Glusose Unit: | 1.6 |

The substituted cyclodextrins of the present disclosure can be prepared by using methods for the selective modifications of cyclodextrins, for examples by using methods describe by Khan et al. (Chem. Rev. 1998, 98, 1977-1996). Alternative synthesis routes for the preparation of the substituted cyclodextrins of the disclosure are known to the chemists skilled in the field and broadly described in U.S. Pat. No. 5,710,268; "Advances in cyclodextrin chemistry" by Werz, Vidal, Guiou, Sollogoub, Matthieu, Wiley-VCH Verlag GmbH ed. 2014; and "Modern Synthetic Methods in Carbohydrate Chemistry: From Monosaccharides to Complex Glycoconjugates", Werz, Daniel B.; Vidal, Sebastian, eds, 2014 Wiley-VHC Verlag GmbH.

Once the substituted cyclodextrin is provided, cyclodextrin complexes of odor controlling organic compounds that are active against malodors can be prepared as described supra.

Cyclodextrin Complex Positioning

A cyclodextrin complex of the present disclosure can be disposed in various locations in the absorbent article. The cyclodextrin complex can be simply applied on a surface of the article using any application method. For paper towels, wipes, bath tissue, and facial tissues, a cyclodextrin complex can be applied on any surface of any of the layers making up the article or be mixed with the fibers during the papermaking process.

In the case of absorbent hygienic articles, a cyclodextrin complex can be disposed on the garment-facing side, the body-facing side of the topsheet or absorbent core, or on the body-facing side of the backsheet. Preferably, the cyclodextrin complex is disposed on the absorbent core, and preferably on the body-facing side of the absorbent core. The cyclodextrin complex can also be disposed on other components of the absorbent article, such as the garment-facing side or body-facing side of a secondary topsheet or acquisition layer. A cyclodextrin complex can also be mixed with any of the fibers or materials making up any of the layers of the absorbent article.

The cyclodextrin complex of the present disclosure can be disposed in the absorbent article in or on a layer that is closer to the body-facing surface of the absorbent article than the absorbent core or a layer comprising AGM. In general, for the cyclodextrin complex to effectively release the compound, it should come in contact with moisture. A problem exists when incorporating a cyclodextrin complex in an absorbent hygienic article, because other components, such as the absorbent core and/or superabsorbent material, of the absorbent article have a strong affinity for bodily fluids, including the moisture contained therein. When an absorbent article is insulted with bodily fluid, such as menses or urine, the cyclodextrin complex is thus in competition with the absorbent core and/or superabsorbent material for the moisture contained in the bodily fluid. The absorbent core and/or superabsorbent material has a strong affinity for the moisture and once the absorbent core and/or superabsorbent material contacts the bodily fluid, the absorbent core and/or superabsorbent material effectively "lock-up" the moisture of the bodily fluid, thereby reducing the amount of moisture available to contact the cyclodextrin complex and release the compound to provide odor control benefits. Surprisingly, it has been discovered that if the cyclodextrin complex is coated onto the outside surface of the AGM particle, that this can actually speed activation and release of the cyclodextrin and fragrance complex. Without being bound by theory, it is believed that the high solubility of the complexes of the present disclosure and the relatively slow kinetic of absorption by the AGM particles allow the complete dissolution of the complexes before the AGM granule is able to compete for the liquid absorption and the location of the cyclodextrin complex on the surface of the AGM granule provides for a complete release exactly when and where it may be needed (i.e., where a possible malodorant liquid is present). This results in more effective release of the complexed odor controlling organic compounds and provides improved odor control benefits.

In the case of catamenial tampons, the cyclodextrin complex can be present on, or in, any component of the tampon, including the absorbent compressed pledget forming the tampon body, the overwrap, and the extraction cord. If a secondary mass of absorbent material is present along the extension cord proximate to the extraction end of the tampon, the cyclodextrin complex can be comprised within the secondary mass.

In all cases the cyclodextrin complex of this disclosure can be applied to any of the layers comprising an absorbent article in powder form or as a liquid or semi-solid carrier and applied as a lotion. Cyclodextrin complexes can be dispersed in a carrier to form a dispersion and then applied to an absorbent article. The carrier can be selected for example from the group consisting of polysiloxane oil, mineral oil, petrolatum, polyethylene glycol, glycerin, and mixtures thereof. The carrier can be polysiloxane oil such as a silicone glycol copolymer (Dow Corning 190 Fluid). The dispersion can be applied using conventional glue application equipment such as a slot coater to provide striped patterns, or air assisted applicators for patterned applications (e.g., spray, spiral, serpentine, fibrils, omega, signature, and the like). Patterned applications can be preferred because the complex can be applied and not impact fluid acquisition. Providing a pattern having a large void space can allow fluid penetration on the sides. Patterned applications can allow a precise application and avoid contact with a glue used to connect the various layers of the absorbent article.

A method to applying a cyclodextrin complex into an absorbent article forms the complex directly at the site of application. This is because substituted cyclodextrins can have improved solubility both in water and in ethanol-based solvents. This improved solubility can allow the preparation cyclodextrin complexes at the application site (e.g., on a layer of material that is part of an absorbent article) using a method that is ineffective with unsubstituted cyclodextrins which have a lower solubility. Here, the substituted cyclodextrin is solubilized in a solvent system comprising at least 60%, or at least 80%, or at least 95% of volatile solvents (e.g., water, $C_1$-$C_8$ alcohols, $C_1$-$C_8$ ketone and aldehydes, $C_1$-$C_8$ hydrocarbons, supercritical fluids, or even cooled gases in fluid form (e.g., liquid nitrogen, ethanol, or mixtures thereof) together with an odor controlling organic compound forming a solution.

The solvent system can comprise less than 5%, or less than 1.0%, or less than 0.5% of any non-volatile solvent(s) having a C Log P value less than 3 because they can interfere negatively with the crystallization of the CD complex.

The viscosity of the solution can be adjusted to be easily pumpable or sprayable. The viscosity can be less than 60 cp at 20° C., or less than 40 cp at 20° C. (Brooksfield viscosity, measured at 20 $sec^{-1}$ and spindle 40 mm SST HB ST). Viscosity can be lowered by diluting the solution. If solutions are prepared ahead of time and water is used in combination with ethanol, than the ratio of water to ethanol can be selected to prevent the formation of microbial growth in storage. The ratio of ethanol to water can be at least 4/6 by weight. The odor controlling organic compound and the substituted cyclodextrin can be added to this mixture at a molar ratio ranging from between 0.25:1 to 4:1, or from between 0.5:1 to 2:1, or from between 0.8:1 to 1.2:1. The resulting solution can be applied on any substrate making up the absorbent article with any type of applicator for liquid compositions. After application and after evaporation of the volatile solvent, the complex is surprisingly formed in situ without the need of additional carriers for application. The degree of complexing achieved is surprisingly high.

It is believed that when the solvent that dissolves the cyclodextrin derivative evaporates, the cyclodextrin derivative can crystallize into a number of small microcrystals featuring different crystal shapes that do not stack allowing fluid to better penetrate and activate them in use. Crystals can tend to entrap some fibers and therefore bind to a fiber when formed in the presence of a fibrous substrate. This can be advantageous because the loss of the odor controlling organic compound is prevented and positioning and dosing is facilitated as the complex forms and remains in the place where the solution is applied.

It can be preferred that the volatile solvent evaporate as much as possible during manufacturing before the products are sealed into air tight plastic bags. If required, articles can be heated during manufacturing to facilitate evaporation of the solvent.

When the cyclodextrin complex is introduced into the absorbent article as a coating on AGM particles, the coating can be obtained by depositing and evaporating a solution comprising the cyclodextrin and the one or more odor controlling organic compound as described above in the case of the application to any other layer or material of the absorbent article. Any coating method can be used.

Precisely coated AGM granules can be obtained during the production of the absorbent article by spraying or otherwise depositing a solution comprising cyclodextrin and one or more odor controlling organic compounds dissolved in solvent as described supra onto the surface of the AGM during assembly before or after application within the absorbent article (i.e., AGM can be treated with the cyclodextrin complex solution when still in the drum, before application to the absorbent article, or after having been deposited onto the absorbent article).

Alternatively pre-coated AGM granules can be directly prepared in advance (e.g., directly by an AGM supplier and directly dosed during production of the absorbent article). This can be advantageous by not having to control solvent evaporation during article production, especially if the article is manufactured at high speed and then packaged in an air-tight package.

Any suitable method of coating or application to the outside surface can be used. One method sprays a mist of the dissolved cyclodextrin solution, odor controlling organic compound(s), and solvent onto a dry AGM particle surface. The AGM particle can be dried to less than about 20% moisture or less than 10% moisture. Alternatively, the outside surface of the AGM particle can be coated using a Wurster spray coater. Alternatively, a solution can be sprayed on to a moving bed of dry AGM particles using a mist or spray applicator capable of creating a droplet size less than about half the size of the AGM particle. Alternatively coated AGM particles can be obtained by rapidly dipping a bed of AGM particles into a tank of a solution of dissolved cyclodextrin, odor controlling organic compound(s), and solvent, and removing it immediately thereafter to coat the outside surface without swelling the AGM particle. Drying steps can follow techniques common in the art. It can be preferred that any process that achieves effective AGM particle coating is suitable when done in a manner that limits the quantity of water or other fluid contact that can swell the AGM particle.

Generally, it can be preferred to apply a coating that results in a perfume having an AGM weight ratio ranging from between 1:100 to 1:1000. The one or more odor controlling compound is typically comprised into an absorbent article in an amount of from about 0.01 to about 1000 milligrams per absorbent article, in some embodiments from about 0.1 to about 100 milligrams per absorbent article, or from about 0.1 to about 500 milligrams per absorbent article.

The described process can be applicable to any absorbent article with the amount of the one or more odor controlling compound applied as required according to the size of the absorbent article. The effectiveness of the odor control technology of the present disclosure is higher than previous absorbent article odor control technologies. Surprisingly, less odor control compounds can be used to achieve effective odor control as tabulated below. This benefit can reduce contact dermatitis and skin irritation. This can be especially important for skin sensitive populations such as premature infants and incontinent adults where skin barrier function may already be compromised from chronic hyper-hydration and/or occlusion).

Table 1 provides examples of personal hygiene absorbent articles and target add-on amounts of one or more odor controlling compounds. The weight indicated only refers to the one or more odor controlling compound and excludes any cyclodextrin used for complexing.

TABLE 1

Odor Controlling Compound Target Add-on Amount Ranges

| Absorbent article | Range (in mg) Min | Max |
|---|---|---|
| Panty-Liners | 0.05 | 5 |
| Sanitary Napkins | 0.05 | 20 |
| Adult incontinence pads | 0.05 | 30 |
| Adult incontinence Diapers | 0.05 | 50 |
| Baby Diapers | 0.05 | 50 |
| Tissue paper (roll) | 0.05 | 20 |

Any odor controlling organic compound that forms stable complexes with cyclodextrin can be used. Further, a single odor controlling organic compound can be used or combinations of more odor controlling organic compounds can be used. Examples of suitable odor controlling organic compounds are detailed in lists (a/a*), (b), (c), (d), and (e) provided infra. It can be preferred that at least one reactive compound from lists (a/a*) or (b) is present.

List (a) includes reactive compounds having a "thiol vapor pressure suppression index" (TVPS) of more than 20. The thiol vapor pressure suppression (TVPS) index is a measure of the reduction in butanethiol concentration in the headspace of a compound as measured using a fast GC instrument (e.g., the zNose 7100 from Electronic Sensor Technologies, Newbury Park, Calif.).

Examples of preferred reactive compounds suitable for the present disclosure and have a TVPS higher than 20 are provide as a list infra (a*). These exemplary compounds not only have a TVPS higher than 20 but also form complexes with cyclodextrin which are particularly stable and release the complexed materials when needed. Exemplary compounds (a*) include melonal, adoxal, trans-2-hexenal, ligustral, Floral Super, Florhydral, 5-methyl-2-thiophene-carboxaldehyde, hydratropic aldehyde, undecenal, 9-undecenal, 10-undecenal, trans-4-decenal, cis-6-nonenal, isocyclocitral, precyclemone b, (E)-2,(z)-6-nonadienal, undecyl aldehyde, methyl-octyl-acetaldehyde, Lauric aldehyde, silvial, vanillin, floralozone, and combinations thereof. The compounds in list (a/a*) are particularly reactive toward malodorant molecules containing Sulfur atoms (e.g., thiol type malodors typically associated with protein degradation in menstrual fluids, feces, food, and the like).

Additional reactive aldehydes and/or ketones which can be advantageously used include the following listed in list (b): hexyl cinnamic aldehyde, alpha-amylcinnamic aldehyde, p-anisaldehyde, benzaldehyde, cinnamic aldehyde, cuminic aldehyde, decanal, cyclamen aldehyde, p-t-butyl-alpha-methyldihydrocinnamaldehyde, 4-hydroxy-3-methoxycinnamaldehyde, vanillin isobutyrate, 2-phenyl-3-(2-furyl)prop-2-enal, ethyl vanillin acetate, vanillin acetate, heptanal, lauryl aldehyde, nonanal, octanal, phenylacetaldehyde, phenyl propyl aldehyde, salycil aldehyde, citral, 2,4-dihydroxy-3-methylbenzaldehyde, 2-hydroxy-4-methylbenzaldehyde, 5-methyl salicylic aldehydes, 4-nitrobenzaldehyde, o-nitrobenzaldehyde, 5-ethyl-2-thiophenecarbaldehyde, 2-thiophenecarbaldehyde, asaronaldehyde, -(hydroxymethyl)-2-furaldehyde, 2-benzofurancarboxaldehyde, 2,3,4-trimethoxybenzaldehyde, protocatechualdehyde, heliotropine, 4-ethoxy-3-methoxy benzaldehyde, 3,4,5-trimethoxybenzaldehyde, 3-hydroxybenzaldehyde, o-methoxycinnamaldehyde, 3,5-dimethoxy-4-hydroxycinnamaldehyde, 2,8-dithianon-4-3n-4-carboxaldehyde, sorbinaldehyde, 2,4-heptadienal, 2,4-decadienal, 2,4-nonadienal, 2,4-nonadienal, (E,E)-,2,4-octadien-1-al, 2,4-octadienal, 2,4-dodecadienal, 2,4-undecadienal, 2,4-tridecadien-1-al, 2-trans-4-cis-7-cis-tridecatrienal, piperonylidene propionaldehyde, 2-methyl-3-(2-furyl)acrolein, 2,4-pentadienal, 2-furfurylidene butyrraldehyde, helional, lyral, 3-hexenal, safranal, veratraldehyde, 3-(2-furyl)acrolein, pyruvaldehyde, ethanedial, 1-(2,6,6-trimethyl-1-cyclohexenyl)pent-1-en-3-one; 4-(2,6,6-trimethyl-1-cyclohexen-1-yl)-3-Buten-2-one; 4-(2,6,6-trimethyl-2-cyclohexen-1-yl)-3-buten-2-one, 5-(2,6,6-Trimethyl-2-cyclohexen-1-yl)4-penten-3-one, (E)-4-(2,2-dimethyl-6-methylidenecyclohexyl)but-3-en-2-one, and combinations thereof.

Compounds in list (b) are aldehydes and/or ketones able to react with some classes of malodorant compounds, in particular nitrogen based malodorant compounds, and do not have unpleasant odor.

Reactive compounds in lists (a/a*) and (b) can chemically react with malodorant molecules containing Nitrogen (e.g., amine-type odors derive from the degradation of urine or certain foods like onions) and/or Sulfur (e.g., thiol-type malodors associated with protein degradation in menstrual fluids, feces, food, and the like) Ammonia/amines are one component of malodor associated with the absorption of bodily fluids, such as menses or urine. For example, ammonia/amines are typically present in high amounts in absorbent products used for urine absorption due to the degradation of urea Ammonia/amines and their derivatives can react with aldehydes and/or ketones to form imines (the Schiff base reaction).

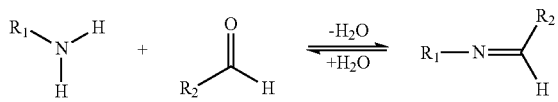

This reaction is catalyzed by enzymes and/or by a slightly acidic pH 4 to 5. The moderate acid requirement can allow protonation of the hydroxyl intermediate to allow water to leave.

Malodorant sulfur based compounds are typically generated by the degradation of proteins (e.g., in menstrual fluids feces or food) and their control can be important in menstrual absorbent articles such as sanitary napkins or panty liners as well as in other absorbent articles that contact proteinaceous materials such food residues or feces. The mechanism of action is believed to be that thiols can react with aldehydes and ketones to form thioacetals and thioketals.

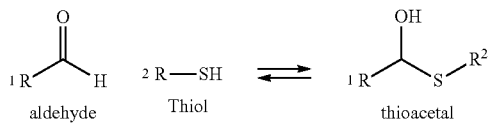

In principle the chemical reactions described above can be obtained from any aldehyde. In practice the reactivity of aldehydes in these reactions and in the specific context of an absorbent article can be different. The reactive compounds (a) and (b) of the present disclosure are effective in reacting with Nitrogen based malodorant molecules and those according to (a) are particularly effective in reacting also with sulfur based malodorant molecules. The particularly high reactivity of these reactive compounds towards sulfur based malodorant molecules can render them effective for use in absorbent articles used to absorb menses. Further, the reactive compounds of the present disclosure can be particularly advantageous in the specific context of absorbent articles because they have a pleasant and low intensity odor, are able to be complexed effectively, and can be quickly released when needed.

Another aspect of the present disclosure is that each complexed reactive compound can have an individual odor characteristic. Therefore their introduction within an absorbent article can provide not only reactivity on malodors but also individual fragrant notes that can be combined with other odorous components (encapsulated/complexed and/or in free uncomplexed form) allowing the formulator to obtain a broader range of fragrances to be released by the product when used (i.e. when the complexed reactive compound is activated).

Other odor controlling organic compounds which can be used herein include particular other fragrance/masking/reacting components selected from the lists (c), (d) and (e).

Components from list (c) include menthol, menthyl acetate, menthyl lactate, menthyl propionate, menthyl butyrrate, menthone, mint terpenes, laevo-carvone, Cis-3-Hexenol & Cis-3-Hexenyl acetate, koavone, methyl dioxolan, ethylene brassylate, and salycilate esters. Salycilate esters are preferably selected from amyl salicylate, isoamyl salicylate, isobutyl salicylate, cis-3-hexenyl salicylate, hexyl salicylate, cyclohexyl salicylate, benzyl salicylate, phenylethyl salicylate, propyl salicylate, isopropyl salicylate, and combinations thereof.

These are all compounds that can mask malodors. Masking may occur through vapor pressure suppression of the malodor or by overwhelming the unpleasant malodor with the pleasant odor of the fragrance component. These materials, when used, may significantly reduce the ability to detect malodors. The masking ability to hide malodors is possible due to the volatile nature of the materials selected, which are released from the complex in the absorbent article and are then inhaled into the nose of a consumer, generally within somewhat close range of the absorbent article, e.g. within about 0 to 10 meters of the article by normal breathing (although this should in no way be intended to limit the scope of the disclosure).

Components from list (d) include methyl-dihydrojasmonate, methyl jasmonate, eucalyptol, tetrahydro-linalool, phenyl-ethyl alcohol, hexyl iso-butyrate, linalyl acetate, benzyl acetate, Benzyl alcohol, and combinations thereof. These volatile materials are well complexed with cyclodextrin and can be released very quickly upon contact with a water based liquid. The absorbent article can respond even more quickly to an insult of malodorant liquid by releasing a compound having a good general masking effect against malodors. A volatile material reduces the vapor pressure of other malodorant compounds by slowing down their evaporation rate.

List (e) includes other malodor masking and fragrance components which can be used as odor controlling organic compounds. The list includes camphor, p-menthane, limonene, cresol, linalool, myrcenol, tetra hydromyrcenol, di-hydromyrcenol, myrcene, citronellol, citronellyil derivatives, geraniol, geranyl derivatives, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, camphene, citronellal, hydroxycitronellal, ethyl maltol, methyl phenyl carbinyl acetate, dihydrocumarin, di-hydromyrcenyl acetate, geraniol, geranial, isoamylacetate, ethyl, and/or triethyl acetate, para-cresol, para-cymene, methyl abietate, hexyl-2-methyl butyrate, hexyl-2-methyl butyrate, and combinations thereof.

All compounds discussed herein include their isomeric forms, diastereomers, and enantiomers unless a specific isomeric form is specified. Further, the same component can be considered both a malodor reactive component, a malodor masking component, and/or a fragrance component.

When one or more odor controlling organic compounds are present, the complex can be prepared by mixing all compounds together before preparing the complex. Alternatively, cyclodextrin complexes containing only one or some compounds can be prepared separately and mixed according to the desired dosages before placement into the absorbent article. Additionally, the components from lists a), b), c), d) and e) in complexed form may also include components from the same lists or other fragrance components in free or in encapsulated form.

The absorbent article may exhibit no noticeable, or little, scent before use. Therefore, no, or a small level of, fragrant compounds may be present and the complexed compounds can be complexed efficiently and completely so that only a low amount of free components are present before product usage and are released only during use of the absorbent article.

The present disclosure further provides a method for reducing malodor associated with malodorant fluids comprising the step of contacting the fluid with an absorbent article of the present disclosure. The method can reduce the malodor associated with the malodorant fluids. The present disclosure also provides exemplary methods for making absorbent articles comprises the step of applying a cyclodextrin complex onto one of the materials comprising the article.

Process

Exemplary, but non-limiting, processes for producing coated swellable materials having an odor active coating comprising the encapsulated products of the present disclosure disposed upon a surface thereof can be produced as described infra.

Example 1

A first exemplary process for providing water swellable material comprising a water activated coating in accord with the present disclosure uses a fluidized bed or Wurster Coater.

For example, a GLATT ProCell granulator-coater with GF3 process vessel may be used (supplier by Glatt Ingenieurtechnik GmbH, Nordstrasse 12, 99427 Weimar, Germany). It can be desirable that the equipment is pre-heated, for example to 50° C. under nitrogen flow for about 30 mins.

Between 250 g and 2 kg, (e.g., 500 g of AGM) is placed in the vessel. The coating agent, preferably in fluid form, is placed in a container on a stirring platform and stirred using a magnetic bar at low speed to prevent entrainment of air. The weight is of AGM used is recorded.

Approximately 9.26 g of coating agent is added to the vessel containing fluid AGM. The composition of the coating agent is preferably Ethanol (76.544% by weight), water (19.136% by weight), methyl-BCD (3.78% by weight), NSH705-2 perfume (0.54% by weight). The preferred gas for fluidization is nitrogen. The coating liquid contains ethanol, and hence, the gas inside the vessel maybe flammable if oxygen is present.

The peristaltic pump is calibrated and then set to the desired flow rate (2 g/min) and the direction of flow of the coating agent is set forward. The desired nitrogen inlet flow and temperature are set (e.g., 55 m$^3$/hr to enable good fluidization and mixing in the vessel and a temperature between 40° C. and 80° C., preferably 55° C.). Then the atomizing air supply and the pump are started. The experiment is typically completed when the coating agent in the container is empty and all the coating agents inside the pump and hoses are also emptied.

The flow rate of the coating agent and the temperature are set such that the water swellable hydrogel is not getting sticky and no additional drying is needed. The coating liquid is preferably sprayed with a two-stream nozzle. Nitrogen is used as a gas to prevent risk of explosion due to ethanol containing coating agent. The fluidized bed may also be operated in a continuous process mode.

Example 2

A second exemplary process for providing water swellable material comprising a water activated coating in accord with the present disclosure uses a Ploughshare Mixer. This exemplary process can utilize a Lödige ploughshare mixer L5 (Gebrüder Lödige Maschinebau GmbH, Elsener Strasse 7-9, 33102 Paderborn, Germany).

It is preferred that the equipment is pre-heated, for example to 40° C., for example for about 30 mins. Between about 300 g and 2 kg, preferably 500 g of AGM, is placed inside the vessel. The composition of the coating agent is preferably Ethanol (76.544% by weight), water (19.136% by weight), methyl-BCD (3.78% by weight), NSH705-2 perfume (0.54% by weight).

A desired amount of coating agent, preferably in fluid form, is placed in a container on the stirring platform and stirred using a magnetic bar at low speed to prevent entrainment of air. The weight can be recorded. The container is filled with the coating agent.

The mixing vessel is filled with nitrogen gas. The coating liquid contains ethanol, and hence, the gas inside the vessel maybe flammable if oxygen is present. For the spray nozzle, also Nitrogen is used. The peristaltic pump is calibrated and then set to the desired flow rate (2 g/min) and the direction of flow of the coating agent is set forward.

After application of the coating liquid, the ploughshare mixer is runs for an additional 30 min or until the coating agent is fully vaporized. After coating agent addition and drying is completed, the bottom outlet of the vessel is opened and the coated material discharged. It is preferred to store the material in airtight container.

Thiol Vapor Pressure Suppression Index (TVPS) Test Method

The thiol vapor pressure suppression index (TVPS) measurement is conducted as follows:

Before any measurements the instrument is calibrated according to manufacturer's instructions under the same experimental settings. The instrument has a DB-5 column (EST Part No. SYS7100C5, Electronic Sensor Technologies, Newbury Park, Calif.) 1 m in length, 0.25 µm phase thickness, and 0.25 mm in diameter. The experimental settings for TVPS measurements are:

Sampling time: 10 s
Sensor Temperature: 40° C.
Initial Column Temperature: 40° C.
Inlet Temperature: 40° C.
Valve Temperature: 40° C.
Column Temperature Ramp Rate: 10° C./s
Final Column Temperature: 200° C.

TVPS of a compound is measured as follows: 100 µl±1 µl of a 1% v/v butanethiol (99%, purity) solution in ethanol (200 proof) is added into a 1 ml vial (8×40 mm). These vials are borosilicate glass straight walled vial. A suitable butanethiol is item 112925 from Sigma-Aldrich (Sigma-Aldrich, St. Louis, Mo.). In another 1 ml vial (8×40 mm), 5 5 µl±0.2 µl of the compound is added. Both open vials are then placed inside a 20 ml headspace vial (22×75 mm), and the vial is immediately sealed using a screw thread closure with PTI-B/Silicone septa. The vial is heated to 37° C. for 4 hours. After 4 hours, the vial is removed from the oven and let to equilibrate at 25° C.±2° C. for 15 minutes. The headspace inside the vial is sampled using the zNose following the experimental protocol outlined above. Samples with butanethiol alone, and the volatile active alone, are run using the same protocol to identify the peaks for both materials.

An acceptable retention index for butanethiol is 720±30. If the peaks butanethiol peak and the volatile material peak co-elute, one skilled in the art can modify the protocol settings to separate those peaks. A minimum resolution of 1.5 should be obtained. For example one can change the column temperature ramp rate. In between samples, the instrument needs to be cleaned to remove any trace materials. To clean the instrument, the instrument is run without samples as needed until no peaks greater than 100 counts are observed.

The amount of butanethiol in the headspace is measured from the area of the peak on the chromatograph for butanethiol ($A_{BtSH,Rx}$). To calculate the percentage of butanethiol reduction in the headspace, a control with the butanethiol solution without the volatile material is run in the same manner and the area is measured as well ($A_{BtSH,C}$). TVPS is then measured as the percentage reduction in butanethiol area calculated using the following formula:

$$TVPS = \frac{A_{BtSH,c} - A_{BtSH,Rx}}{A_{BtSH,C}} \times 100$$

TABLE 2

Exemplary measurements obtained by TVPS

| Sample | Butanethiol Peak Retention Index | Area (counts) |
|---|---|---|
| Butanethiol Control<br>Vial 1: 100 µl of 1% v/v butanethiol in ethanol<br>Vial 2: Empty | 720 | $A_{BtSH, C}$ = 4934 |
| Butanethiol + Florhydral<br>Vial 1: 100 µl of 1% v/v butanethiol in ethanol<br>Vial 2: 5 µl Florhydral | 720 | $A_{BtSH, Rx}$ = 2442 |

An exemplary TVPS calculation for TVS provides:

$$TVPS = \frac{4934 - 2442}{4934} \times 100 = 50.5\%$$

The TVPS values for several compounds described supra are provided in Table 3. TVPS for the compounds indicated with (*) have been approximated using a mathematical model calculated starting from real measurements on a large number of compounds. The model is created using the QSAR software CAChe ProjectLeader WorkSystem Pro 7.1. Using the molecular structure from the compounds for which TVPS was evaluated, several molecular properties are calculated. A regression algorithm is the used to calculate the best fit to predict TVPS based on the 4 molecular descriptors that best fit the data. The model is then used to predict TVPS for other compounds using the same software. The values of TVPS approximated with the molecular modeling system are presented for illustration only, for the avoidance of doubt it is specified that the TVPS values provided in Table 3 for use in the present disclosure are only the TVPS values measured with the zNose analytical method described above.

TABLE 3 zNose Measured TVPS Values

| | TVPS |
|---|---|
| melonal | 20.4 |
| adoxal | 24.4 |
| trans-2-hexenal | 27.1 |
| ligustral | 42.5 |
| Floral Super | 52.4 |

TABLE 3-continued zNose Measured TVPS Values

| | TVPS |
|---|---|
| Florhydral | 53.3 |
| 5-methyl-2-thiophene-carboxaldehyde | 67.4 |
| hydratropic aldehyde(*) | 72.0 |
| Undecenal(*) | 26.2 |
| 9-undecenal(*) | 67.5 |
| 10-undecenal(*) | 52.0 |
| trans-4-decenal(*) | 60.3 |
| cis-6-nonenal(*) | 57.1 |
| isocyclocitral(*) | 51.4 |
| precyclemone b(*) | 40.7 |
| (E)-2-(z)-6-nonadienal(*) | 35.8 |
| undecyl aldehyde(*) | 34.9 |
| methyl-octyl-acetaldehyde(*) | 30.2 |
| Lauric aldehyde(*) | 26.6 |
| silvial(*) | 25.8 |
| vanillin(*) | 23.7 |
| floralozone(*) | 23.5 |
| Hexylcinnamic aldehyde | 8.0 |
| neral | 17.1 |
| ethyl vanillin | 2.9 |

Comparison of Fragrance Release of Different Methyl Substituted β-Cyclodextrin

To demonstrate the perfume release effectiveness of different methyl substituted, β-Cyclodextrin (available from TCI America, OR, or equivalent), 2,6-Di-O-methyl-β-cyclodextrin (available from Acros Organics, NJ or equivalent), and 2,3,6-Tri-O-methyl-β-cyclodextrin (available from TCI America, or equivalent) were each complexed with a model blend of Odor Controlling Organic Compounds (indicated with the acronym OCOC) and spiked onto a portion of an ultra, feminine hygiene pad (a suitable pad is Always Ultra® by Procter and Gamble®, or equivalent). After dosing with water, the headspace was sampled using Solid Phase Micro-Extraction (a suitable fiber assembly is a 2 cm Stableflex 24 Ga, 50/30 µm DVB/CAR/PDMS available from Supelco, Pa. or equivalent) followed by gas chromatography/mass spectrometry (a suitable unit is the 5977A Mass Selective Detector (MSD) also available from Agilent, or equivalent) with a GERSTEL Multipurpose Sampler (Gerstel, Liticumo, Md. or equivalent) to quantify the OCOC release. The model OCOC used is a neat mixture of benzaldehyde (1.6 g, 15.08 mmols), ligustral (1.6 g, 11.58 mmols), citral (1.6 g, 10.51 mmols), cinnamic aldehyde (1.6 g, 12.11 mmols), and florhydral (1.6 g, 8.41 mmols) (all available from Sigma Aldrich or equivalent). The mixture is homogenized before use.

The Standard Pad Substrates are prepared by cutting a 10 cm lateral strip across the whole product centered at the longitudinal center of an Always Ultra® normal size pad.

A mixture of the model OCOC for each β-cyclodextrin type was solubilized in water at a one-to-one molar ratio (β-cyclodextrin/OCOC). The amount of water used for the complexation was adjusted for each β-cyclodextrin type according to its individual water solubility to ensure complete dissolution of the β-cyclodextrin complex. Each mixture of β-cyclodextrin and OCOC in water was thoroughly homogenized. Solutions of β-cyclodextrin, OCOC, and water were dosed onto a Pad Substrate. An amount of solution was added to each pad such that an equivalent of 1 mg of OCOC (complexed by β-cyclodextrin) is available for release upon addition of water. Pads dosed with the above described solution were exposed to open air at room temperature for four days to allow water to evaporate leaving only perfume complexed by β-cyclodextrin. Specifically:

Add 555 mg β-cyclodextrin and 68 mg model OCOC to 30 mL of purified water and mixed thoroughly. 810 µL of this solution (adjusted for losses due to evaporation) is dosed at the longitudinal and lateral center of the pad substrate.

Add 2011 mg 2, 6-di-O-methyl-β-cyclodextrin (38.4%) and 210 mg model OCOC (4%) to 3 mL of purified water and mixed thoroughly. 810 µL of this solution (adjusted for losses due to evaporation) is dosed at the longitudinal and lateral center of the pad substrate. 16 µL of this solution (adjusted for losses due to evaporation) was added to the longitudinal and lateral center of the pad substrate.

Add 1008 mg 2, 3, 6-tri-O-methyl-β-cyclodextrin (4.8%) and 98 mg model OCOC (0.46%) to 20 mL of purified water and mixed thoroughly. 810 µL of this solution (adjusted for losses due to evaporation) is dosed at the longitudinal and lateral center of the pad substrate. 16 µL of this solution (adjusted for losses due to evaporation) was added to the longitudinal and lateral center of the pad substrate.

The control is prepared by dosing 1.0 mg of the neat OCOC at the longitudinal and lateral center of the pad substrate. The control is prepared immediately before dosing with the water The GC analysis was performed on a 30 m long by 0.250 mm diameter column with 5% phenyl arylene methylpolysiloxane phase at a 1 µm film thickness (a suitable column is the DBSMS available from Agilent, or equivalent USP G27 phase). The GC inlet was set at 280° C. in Split-less mode (A CIS-4 SPME low volume glass liner available from Sigma-Aldrich) with a 3 mL septum purge. A 1.5 mL column flow of helium was set at an oven temperature of 150° C. under constant flow conditions. The GC oven was programmed to begin at 150° C. for 1 min, then ramp at 16° C./min to 230° C., hold for 6 min at 230° C., then ramp at 30° C./min to 300° C. and a final hold of 1 min. Upon injection, the SPME fiber is left in the injector for 5.00 min.

The temperature for the MSD transfer line and detector were set to 280° C. and 300° C. respectively. The MSD was configured for electron ionization at −70 eV scanning from 35 m/z to 300 m/z with a scan rate of 192 msec/scan. A Total Ion Chromatogram (TIC) is collected for each specimen. The TIC is then processed to extract ion chromatograms at 106 m/z (benzaldehyde), 67 m/z (ligustral) 69 m/z (citral), 131 m/z (cinnamic aldehyde) and 105 m/z (forhydral). The peaks of interest in the extracted ion chromatogram are integrated and summed.

Each absorbent article Specimens was placed in a 250 mL glass jar and sealed with a PTFE/silicone septum lid (fluoropolymer resin-lined, available from I-CHEM, Thermo Scientific, or equivalent). The pad is positioned along the wall of the jar with the back sheet against the wall. The jar is placed on its side and rotated such that the longitudinal center of the substrate can be dosed with 1.00 mL of purified water. The jar is sealed and the headspace sampled using the SPME for 30 sec at 5, 10, and 30 minute time points after the addition of water. The control is analyzed in like fashion for comparison.

The % Release is based on the summed area of the peaks of interest within the extracted ion chromatogram, normalized to the applied mass of the cyclodextrin: % Release= (Summed Area Counts of β-cyclodextrin/Summed Area counts of control)/mg of β-cyclodextrin dosed on pad In like fashion, three replicates of each β-cyclodextrin complex and control are analyzed and the % Release is calculated for each. The % Release is reported as the arithmetic mean of the three replicates to the nearest 0.1%/mg.

The gravimetric determination of absorption against pressure (AAP) for Polyacrylate Superabsorbent Powders is provided by Nonwovens Standard Procedure NWSP 242.0.R2 (15).

The determination of the permeability dependent absorption under pressure (PDAUP) of saline solution by gravimetric measurement is provided by Nonwovens Standard Procedure NWSP 243.0.R2 (15).

The determination of the fluid retention capacity (FRC) in saline solution by gravimetric measurement following centrifugation for Polyacrylate Superabsorbent Powders is provided by Nonwovens Standard Procedure NWSP 241.0.R2 (15).

The determination of the free swell capacity (FSC) in saline by gravimetric measurement for Polyacrylate Superabsorbent Powders is provided by Nonwovens Standard Procedure NWSP 240.0.R2 (15).

The determination of glass transition temperature, Tg, using Dynamic Mechanical Analysis (DMA) is provided by ASTM method E1640-13.

TABLE 4

Results of Absorption Against Pressure (AAP), Fluid Retention Capacity (FRC), and Free Swell Capacity (FSC) Measured Values and Calculated Efficiencies

| AGM Sample | Perfume in Coating | AAP [g/g] | FRC [g/g] | FRC Efficiency % | FSC [g/g/s] | FSC Efficiency % |
|---|---|---|---|---|---|---|
| AGM 1 with coating | 0.01% NSH 705-2 | 23.1 | 27.3 | 101.1 | 0.3 | 78.9 |
| AGM 1 without coating | | 22.6 | 27.0 | | 0.38 | |
| AGM 2 with coating | 0.01% NSH 705-2 | 22.3 | 28.3 | 99.6 | 0.24 | 88.9 |
| AGM 2 without coating | | 23.2 | 28.4 | | 0.27 | |
| AGM 3 with coating | 0.01% NSH 705-2 | 24.2 | 28.2 | 97.6 | 0.32 | 88.9 |
| AGM 3 without coating | | 24.7 | 28.9 | | 0.36 | |

In a preferred embodiment, the absorbent efficiency can be measured as the Fluid Retention Capacity (FRC) and expressed as the ratio of FRC of the coated AGM (i.e., second absorbent efficiency value or first FRC value) to the un-coated AGM ((i.e., first absorbent efficiency value or second FRC value)) is preferably greater than 0.5 (50%), or greater than 0.6 (60%), or greater than 0.75 (75%), or greater than 0.9 (90%), or greater than 0.95 (95%), or greater than 0.98 (98%), or greater than 0.99 (99%).

In a preferred embodiment, the absorbent efficiency can be measured as the Free Swell Capacity (FSC) and expressed as the ratio of FSC of the coated AGM (i.e., first absorbent efficiency value or first FSC value) to the un-coated AGM ((i.e., second absorbent efficiency value or second FSC value)) is preferably greater than 0.4 (40%), or greater than 0.5 (50%), or greater than 0.6 (60%), or greater than 0.7 (70%), or greater than 0.8 (90%), or greater than 0.85 (85%), or greater than 0.90 (90%).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any disclosure disclosed or claimed herein or that it alone, or in any combination with any other reference or references, teaches, suggests or discloses any such disclosure. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. An absorbent article comprising pre-coated absorbent gelling material particles, said pre-coated absorbent gelling material particles each having an individual coating upon a surface of said pre-coated absorbent gelling material particles wherein said coating comprises microcrystals of a substituted cyclodextrin, wherein the microcrystals comprise an encapsulated compound of one or more odor controlling organic compounds.

2. The absorbent article of claim 1 wherein said encapsulated compound is a water activated/activatable encapsulating compound.

3. The absorbent article of claim 1 wherein said encapsulated compound is further encapsulated with a secondary coating material.

4. The absorbent article of claim 3 wherein said secondary coating material is selected from the group consisting of polysaccharides, natural and artificial/synthetic waxes, esters, ester derivatives, fatty acids, natural, synthetic, and chemically modified lipids, fatty alcohols, linear hydrocarbons, branched hydrocarbons, petrolatum hydrocarbons, enteric coating compositions, polyvinyl alcohols, polyethylene glycols, silicones, surfactants, emulsifiers, polypropylene glycols, cellulose derivatives, glycerin, mono- glycerides, di-glycerides, polyglycerol esters, polyglycerol emulsifiers, and mixtures thereof.

5. The absorbent article of claim 1 wherein the substituted cyclodextrin comprises a cyclodextrin (wherein the H atom of OH groups in positions 2, 3 and 6 is partially or entirely replaced by a substituent —R) having a substitution degree (DS) of 0.4 or more —R substituents per molecule of cyclodextrin.

6. An absorbent article according to claim 5 wherein the substituted cyclodextrin has a substitution degree ranging from about 0.4 to about 2.5.

7. An absorbent article according to claim 6 wherein said substitution in position 2 is between 20 and 90%.

8. An absorbent article according to claim 6 wherein said substitution in position 6 ranges from between about 20% and about 90%.

9. An absorbent article according to claim 6 wherein said substituted cyclodextrin is selected from the group consisting of alpha-cyclodextrin, beta-cyclodextrin, gamma-cyclodextrin, and combinations thereof.

10. An absorbent article according to claim 6 wherein said —R substituents are selected from the group consisting of a linear C1-C5 saturated chain, a branched C1-C5 saturated chain, and combinations thereof.

11. An absorbent article according to claim 6 wherein said —R substituents are selected from the group consisting of methyl, hydroxymethyl, and combinations thereof.

12. The absorbent article of claim 5, wherein substitution in position 3 is greater than zero.

13. The absorbent article of claim 12, wherein substitution in position 2 is 20% or above, in position 6 is 20% or above, and in position 3 is 50% or below.

14. The absorbent article of claim 1, wherein the one or more odor controlling organic compounds comprises a perfume, wherein the coating results in the perfume having an absorbent gelling material weight ratio of from about 1:100 to about 1:1000.

15. The absorbent article of claim 1, wherein the substituted cyclodextrin comprises a cyclodextrin (wherein the H atom of OH groups in positions 2, 3 and 6 is partially or entirely replaced by a substituent —R) having a substitution degree (DS) of about 0.4 to about 2.5 or more —R substituents per molecule of cyclodextrin; wherein the —R substituents are selected from the group consisting of a linear C1-C5 saturated chain, a branched C1-C5 saturated chain, and combinations thereof; wherein substitution in position 2 is 20% or above, in position 6 is 20% or above, and in position 3 is 50% or below.

* * * * *